United States Patent
Das et al.

(10) Patent No.: US 9,629,585 B2
(45) Date of Patent: Apr. 25, 2017

(54) WEARABLE PATCH COMPRISING MULTIPLE SEPARABLE ADHESIVE LAYERS

(71) Applicant: ZANSORS LLC, Tysons, VA (US)

(72) Inventors: Ranjit Das, Gaithersburg, MD (US); Mark Travaglini, Northville, MI (US)

(73) Assignee: ZANSORS LLC, Tysons, VA (US)

( * ) Notice: Subject to any disclaimer, the term of this patent is extended or adjusted under 35 U.S.C. 154(b) by 0 days.

(21) Appl. No.: 14/023,560

(22) Filed: Sep. 11, 2013

(65) Prior Publication Data

US 2014/0012102 A1    Jan. 9, 2014

Related U.S. Application Data

(60) Provisional application No. 61/699,790, filed on Sep. 11, 2012.

(51) Int. Cl.
*A61B 5/00* (2006.01)
*A61B 5/08* (2006.01)
(Continued)

(52) U.S. Cl.
CPC .......... *A61B 5/6833* (2013.01); *A61B 5/0022* (2013.01); *A61B 5/08* (2013.01); *A61B 5/11* (2013.01); *A61B 5/145* (2013.01); *A61B 5/6801* (2013.01); *A61F 13/00051* (2013.01); *A61F 13/02* (2013.01); *A61F 13/025* (2013.01); *A61F 13/0246* (2013.01); *A61K 9/703* (2013.01); *A61B 5/113* (2013.01); *A61B 5/1118* (2013.01); *A61B 5/4806* (2013.01); *A61B 5/4818* (2013.01);
(Continued)

(58) Field of Classification Search
CPC ........... A61B 5/00; A61B 5/01; A61B 5/0002; A61B 5/021; A61B 5/1455; A61B 5/14551; A61B 5/14532; A61B 5/6831; A61B 5/6833; A61B 5/4266; A61B 5/4818
USPC ....... 600/300, 301, 309, 310, 322, 323, 324, 600/340, 345, 362, 382, 386, 392, 412, 600/437, 473, 476, 500, 529, 544, 546, 600/549; 374/141; 604/307
See application file for complete search history.

(56) References Cited

U.S. PATENT DOCUMENTS 4,426,884 A   1/1984   Poichaninoff
4,641,643 A   2/1987   Greer
(Continued)

OTHER PUBLICATIONS

"Wireless Sensor Systems for the Medical Ward of the 21st Century" (http://www.enel.ucalgary.ca/People/Haslett/WCLM/CCHE/WebPage/AdHoc.html).*
(Continued)

*Primary Examiner* — Eric Winakur
*Assistant Examiner* — Chu Chuan (JJ) Liu
(74) *Attorney, Agent, or Firm* — DLA Piper LLP US; Nicholas Panno

(57) ABSTRACT

Wearable patches comprising multiple separable adhesive layers. One or more of the layers can comprise electronics, mechanical components, gauze, medicine and/or other types of hardware suitable for the intended use of the patch. In use, a first layer of the patch is adhered to a user. When it is time to change layers, the patch is removed from the user, the first layer is removed from the patch to expose a second adhesive layer, and the second layer is applied to the user. The process may be repeated until the remaining layers of the patch have been used.

24 Claims, 1 Drawing Sheet

(51) Int. Cl.
  *A61B 5/11* (2006.01)
  *A61B 5/145* (2006.01)
  *A61F 13/02* (2006.01)
  *A61K 9/70* (2006.01)
  A61M 35/00 (2006.01)
  A61B 5/113 (2006.01)
  A61F 13/00 (2006.01)

(52) U.S. Cl.
  CPC ... *A61B 2503/04* (2013.01); *A61B 2560/0412* (2013.01); *A61F 2013/0094* (2013.01); *A61M 35/00* (2013.01)

(56) References Cited

U.S. PATENT DOCUMENTS

| | | | | |
|---|---|---|---|---|
| 5,061,258 | A * | 10/1991 | Martz | 604/307 |
| 5,797,867 | A | 8/1998 | Guerrera et al. | |
| 6,113,539 | A * | 9/2000 | Ridenour | A61B 5/0002 600/309 |
| 6,160,196 | A * | 12/2000 | Knieler et al. | 602/48 |
| 7,113,815 | B2 | 9/2006 | O'Neil et al. | |
| 7,206,630 | B1 | 4/2007 | Tarler | |
| 7,219,627 | B1 | 5/2007 | Egloff | |
| 7,499,739 | B2 * | 3/2009 | Sweitzer et al. | 600/323 |
| 7,894,869 | B2 * | 2/2011 | Hoarau | 600/344 |
| 8,433,383 | B2 | 4/2013 | O'Neil et al. | |
| 8,560,046 | B2 | 10/2013 | Kumar et al. | |
| 8,734,341 | B2 | 5/2014 | Howell et al. | |
| 8,738,112 | B2 | 5/2014 | Choe et al. | |
| 8,852,114 | B2 | 10/2014 | Buxi et al. | |
| 2002/0109600 | A1 * | 8/2002 | Mault et al. | 340/573.1 |
| 2002/0180605 | A1 | 12/2002 | Ozguz et al. | |
| 2004/0208916 | A1 * | 10/2004 | Abbott et al. | 424/449 |
| 2005/0096513 | A1 | 5/2005 | Ozguz et al. | |
| 2006/0276700 | A1 * | 12/2006 | O'Neil et al. | 600/344 |
| 2007/0206655 | A1 * | 9/2007 | Haslett et al. | 374/141 |
| 2008/0091090 | A1 | 4/2008 | Guillory et al. | |
| 2008/0275327 | A1 | 11/2008 | Faarbaek et al. | |
| 2009/0022941 | A1 | 1/2009 | Fischer et al. | |
| 2009/0054742 | A1 | 2/2009 | Kaminska et al. | |
| 2009/0076346 | A1 | 3/2009 | James et al. | |
| 2010/0274099 | A1 | 10/2010 | Telfort et al. | |
| 2010/0286607 | A1 | 11/2010 | Saltzstein | |
| 2010/0298895 | A1 | 11/2010 | Ghaffari et al. | |
| 2010/0317958 | A1 | 12/2010 | Beck et al. | |
| 2011/0213272 | A1 | 9/2011 | Telfort et al. | |
| 2011/0213274 | A1 | 9/2011 | Telfort et al. | |
| 2011/0279963 | A1 | 11/2011 | Kumar et al. | |
| 2012/0071742 | A1 | 3/2012 | Medina et al. | |
| 2012/0130330 | A1 | 5/2012 | Wilson et al. | |
| 2012/0277549 | A1 | 11/2012 | Libbus et al. | |
| 2013/0053669 | A1 | 2/2013 | Yoo et al. | |
| 2013/0079605 | A1 | 3/2013 | Bandaru et al. | |
| 2013/0245388 | A1 | 9/2013 | Rafferty et al. | |

OTHER PUBLICATIONS

U.S. Appl. No. 14/023,553
International Search Report and Written Opinion from corresponding PCT Application No. PCT/US2013/059125 dated Jan. 22, 2014.
Office Action from corresponding U.S. Appl. No. 14/023,553 dated Jan. 15, 2014.
International Preliminary Report on Patentability from PCT/US2013/059125 dated Mar. 17, 2015.
U.S. Appl. No. 14/023,553.

* cited by examiner

WEARABLE PATCH COMPRISING MULTIPLE SEPARABLE ADHESIVE LAYERS

CROSS REFERENCE TO RELATED APPLICATIONS

This application claims priority from U.S. Provisional Application Ser. No. 61/699,790 filed Sep. 11, 2012, the entirety of which is incorporated herein by reference.

FIELD OF THE INVENTION

Embodiments of the invention relate to wearable patches comprising multiple separable adhesive layers.

BACKGROUND

Patches that adhere to a person's body are being used for several purposes in today's society. The configuration and use of the patch often depends upon its intended purpose. For example, a patch comprising gauze or other material can be applied to a person to cover a wound and prevent infection (i.e., it is being used as an adhesive bandage). A patch that contains medicine or other substances can be applied to a person to treat a wound or an addiction (e.g., a nicotine patch), or to counteract e.g., sea sickness. Other patches can include electronics such as sensors or integrated circuits to monitor e.g., a person's health or response to physical activity. These patches can also include communication circuitry for communicating data from the patch to an external source.

All of these patches, however, have their shortcomings. For example, single wearable adhesive bandages must be changed frequently, especially if they get wet. In addition, these bandages are contained within individual packaging that must be opened and discarded before the bandage can even be used. Thus, these patches produce packaging waste and are inconvenient for the user because he/she must carry or have access to multiple bandages if they want to properly cover a wound, etc.

Patches that include electronics have additional problems. For example, a single wearable adhesive patch having electronics or other hardware would be used once and discarded, causing all of its electronics/hardware to be discarded even if they are still functional. As can be appreciated, this can be wasteful and expensive, raising the cost of the patches (for both the manufacturer and consumer). To avoid wasting expensive components, and to reduce costs, these patches will sometimes use inferior components that could malfunction, provide low power for its circuitry, and/or low memory storage capacity—all of which are undesirable. Moreover, with single disposable patches, the equipment loses the ability to record/use data from, or share data with, other patches used on the same user, which is also desirable.

Accordingly, there is a need and desire for a better wearable adhesive patch.

SUMMARY

Embodiments disclosed herein provide a wearable patch comprising multiple separable adhesive layers. By stacking multiple layers on top of each other, the same patch can used, removed (e.g., when the user takes a shower or goes swimming) and reapplied without affecting its adhesion to the user (i.e., another adhesive layer can be applied to the user when needed).

One or more of the layers can comprise electronics, mechanical components, gauze, medicine and/or other types of hardware or other substances suitable for the intended use of the patch. In use, a first adhesive layer of the patch is adhered to a user. When it is time to change layers, the patch is removed from the user, the first adhesive layer is removed from the patch to expose a second adhesive layer, and the second adhesive layer is applied to the user. The process may be repeated until the remaining adhesive layers of the patch have been used.

If the adhesive layers contain electronics, data can be passed through the layers to a main processing circuit and memory contained in e.g., a top adhesive layer. This way, the patch has the ability to record/use data from, or share data with, other layers throughout the use of the patch. In addition, the layers can be powered by a single power source in the top adhesive layer or by individual power sources in each layer. Moreover, more expensive and better quality components can be used in the top layer, while disposable components can be used in the lower layers; providing better functionality of the patch circuitry while also reducing its cost because the relatively expensive hardware (that would have been disposed of with each use of a single use patch) is preserved until the lifetime of the multi-layer patch has expired (i.e., all of the layers are used).

DETAILED DESCRIPTION

In the following detailed description, a plurality of specific details, such as types of materials and dimensions, are set forth in order to provide a thorough understanding of the preferred embodiments discussed below. The details discussed in connection with the preferred embodiments should not be understood to limit the claimed invention. Furthermore, for ease of understanding, certain method steps are delineated as separate steps; however, these steps should not be construed as necessarily distinct nor order dependent in their performance.

Figure 1:
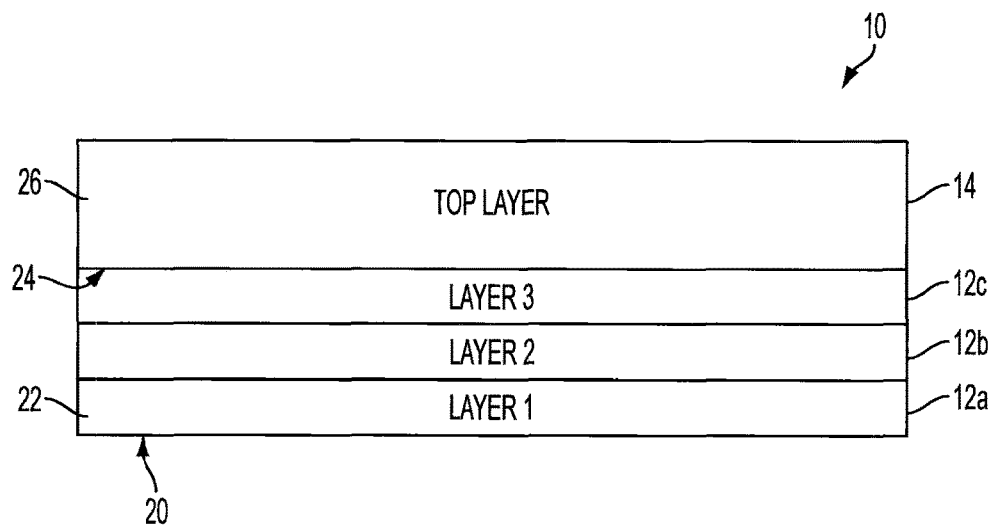
FIG. 1 illustrates an example wearable patch comprising multiple separable adhesive layers in accordance with an embodiment disclosed herein.

FIG. 1 illustrates an example wearable patch 10 comprising multiple separable adhesive lower layers 12a, 12b, 12c and a top layer 14 in accordance with an embodiment disclosed herein. In the illustrated embodiment, there are three lower layers 12a, 12b, 12c and a top layer 14. It should be appreciated that any number of layers can be used and that the disclosed embodiment should not be limited to the number of layers illustrated in FIG. 1. The patch 10 can include as many layers that are practical for the application (e.g., three-day, seven-day, thirty-day patch, etc.). For example, a three-day patch could comprise three separate lower layers 12a, 12b, 12c, one for each day, and a top layer 14 to e.g., protect the adhesiveness of the lower layers 12a, 12b, 12c. If the top layer 14 is constructed the same as the lower layers, then the three-day patch could comprise only two lower layers 12a, 12b for days one and two and the top layer 14 for day three.

Each lower layer 12a, 12b, 12c comprises a substrate 22 having an adhesive 20 formed on one surface. The top layer 14 also comprises a substrate 26 having an adhesive 24 formed on one surface. In one embodiment, when the patch 10 will be applied to a person's body, the substrates 22, 26 comprise white polyethylene foam such as e.g., 1/16", 4# cross linked polyethylene foam. Similarly, when the patch 10 will be applied to a person's body, the substrates 22, 26 are coated with an adhesive 20, 24 such as e.g., an aggressive medical grade pressure-sensitive adhesive (e.g., MA-46 acrylic medical grade adhesive). Although not shown, the adhesive side of one or more layers in the patch 10 may be protected by a liner or release paper such as e.g., a siliconized polycoated release paper (e.g., 84# siliconized polycoated Kraft release paper). The adhesive side of one or more layers in the patch 10 may include the liner, release paper or some other substance that provides quick/easy release/removability of the layer from the patch 10. It should be appreciated that less than all layers may have a liner, release paper, etc. It should be appreciated that the embodiments are not limited to the type of substrate, adhesive or liner (if used) discussed herein and that any suitable substrate, adhesive or liner may be used to form the patch 10.

Although not shown, the substrates 22, 26 can comprise gauze (e.g., the patch 10 is intended to be used as a bandage), medicine (e.g., the patch 10 is intended to be used to apply medicine to treat a wound, infection or a patient's addiction) and/or another substance. An embodiment of a patch 110 that includes electronics or other hardware is discussed below with reference to FIG. 2. In one embodiment, the top layer 14 can comprise a durable coating to provide more protection (e.g., water-proofing) for the other layers 12a, 12b, 12c. It should be appreciated, however, that lower layers 12a, 12b, 12c are protected by the layers above them in the stack of layers 12a, 12b, 12c, 14 and that the durable coating (or other coating) would be providing additional protection. Additionally or alternatively, the top layer 14 can contain a design and/or colors rendering the patch 10 esthetically pleasing to the user and others. For example, the patch 10 can be viewed as a tattoo or other form of body art. Additionally or alternatively, the top layer 14 can comprise padding or another suitable substance to provide protection/comfort to the user in case contact is made to the outside of the patch 10. In addition, although not shown, the substrates 22, 26 can include a tab or other component to help the user separate the layers 12a, 12b, 12c, 14 from each other when it is time to remove a layer and/or the patch 10.

In use, the patch 10 (e.g., a 7-day patch) is removed from its packaging and adhered to the user at the desired location. If the lower layer 12a includes a liner, the liner would be removed before the patch 10 is adhered to the user. After the first intended use of the layer 12a (e.g., after day one, before a shower, etc.), the entire patch 10 is removed, the bottom layer 12a is peeled off and disposed of. The remaining layers 12b, 12c, 14 of the patch 10 should still have fresh adhesive because they are protected by each other and the substrate 26 of the top layer 14. The patch 10 can then be re-adhered to the desired location on the user using the next available adhesive layer (e.g., 12b). This process is repeated for each intended use of the patch. When last usable layer is used, it can be peeled off and disposed of.

As can be appreciated, stacking multiple adhesive layers in one patch 10 creates more convenient user experience and less packaging in comparison to today's wearable patches. In the illustrated embodiment, the patch 10 comprises three lower layers 12a, 12b, 12c and a top layer 14. Existing patches would require four separate packages, creating packaging waste and placing the burden on the user to carry or have access to multiple individual packages.

Although the patch 10 is advantageously used as a bandage or other type of patch applied to a person's body, the patch 10 illustrated in FIG. 1 can be used in many other ways. As such, the illustrated patch 10 is not limited solely to medical use (e.g., bandages, etc.) and/or application to a person's body. For example, the patch 10 can be used as a multiple layer adhesive tape to cover something or hold two or more items together. This would be useful for situations in which the adhesive wears off and a new adhesive tape of the same/similar size is needed.

Figure 2:
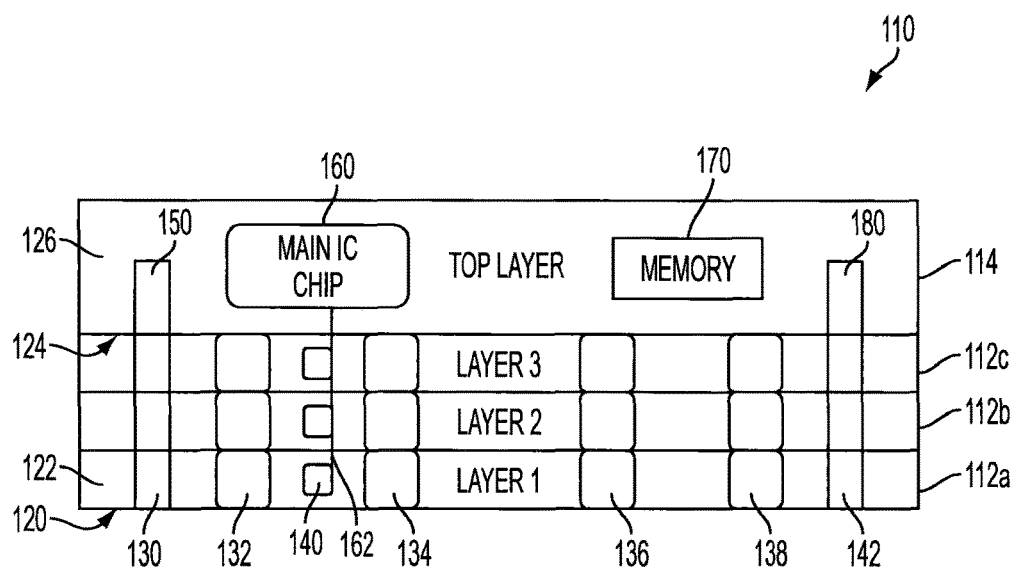
FIG. 2 illustrates another example of a wearable patch comprising multiple separable adhesive layers in accordance with another embodiment disclosed herein.

FIG. 2 illustrates an example wearable patch comprising multiple separable adhesive lower layers 112a, 112b, 112c and a top layer 114 in accordance with an embodiment disclosed herein. In the illustrated embodiment, there are three lower layers 112a, 112b, 112c and a top layer 114. It should be appreciated that, like the patch 10 illustrated in FIG. 1, any number of layers can be used in patch 110 and that the disclosed embodiment should not be limited to the number of layers illustrated in FIG. 2.

Each lower layer 112a, 112b, 112c comprises a substrate 122 having an adhesive 120 formed on one surface. The top layer 114 also comprises a substrate 126 having an adhesive 124 formed on one surface. Although not shown, the adhesive side of one or more layers in the patch 110 is preferably protected by a liner or release paper. The adhesive side of one or more layers in the patch 110 may include the liner, release paper or some other substance that provides quick/easy release/removability of the layer from the patch 110. It should be appreciated that less than all layers may have a liner, release paper, etc. It should be appreciated that the materials used for the substrates 122, 126, adhesives 120, 124 and release paper can be the same as the materials used for the patch 10 illustrated in FIG. 1. It should also be appreciated that the disclosed embodiments are not limited to the type of substrate, adhesive or liner (if used) discussed herein and that any suitable substrate, adhesive or liner may be used to form the patch 110.

In one embodiment, the top layer 114 can comprise a durable coating to provide more protection (e.g., water-proofing) for the other layers 112a, 112b, 112c. Additionally or alternatively, the top layer 114 can contain a design and/or colors rendering the patch 110 esthetically pleasing to the user and others. Additionally or alternatively, the top layer 114 can comprise padding or another suitable substance to provide protection/comfort to the user in case contact is made to the outside of the patch 110. In addition, although not shown, the substrates 122, 126 can include a tab or other component to help the user separate the layers 112a, 112b, 112c, 114 from each other when it is time to remove a layer and/or the patch 10.

As can be seen in FIG. 2, the various layers of the patch 110 include electrical devices (e.g., sensors, microphones, accelerometers) that interface with and/or monitor activity of the person the patch 110 is being applied to; as such, the patch 110 is suitable for use in monitoring e.g., a person's health, sleep patterns or response to physical activity (example uses of the patch 110 and its electronics are discussed below). In addition, the patch 110 could include electronics and components so that it can be used for recreational, fashion or other purposes such as e.g., a watch, smartphone, GPS, skin activated fashion 'mood' device. Furthermore, the patch 110 could include components to measure biological fluids (e.g., blood, hormones); for example, a person can wear a patch 110 to measure insulin or cardiac markers for heart attack (troponin). This allows the user to wear patches to measure biological fluids sub-cutaneous or trans-dermal. With no external wiring, the patch 110 can be worn while the user showers. According to the illustrated embodiment, each lower layer 112a, 112b, 112c comprises a power component 130 (e.g., a battery or a connection to a power component 150 in the top layer 114), one or more sensors 132, 134, 136, 138, an integrated circuit (IC) chip (or circuit) 140 and a data bus portion 142. The sensors 132, 134, 136, 138 could be microphones, accelerometers, pressure sensors for sensing the wearer's pulse, humidity sensors for measuring sweat, temperature sensors for measuring heat, altimeters for measuring incline, and electrical sensors for measuring electrical heartbeats. In addition, the sensors 132, 134, 136, 138 can comprise more complex (higher order) sensors based on micro-electro-mechanical systems (MEMS) sensors or even microfluidic sensors. The illustrated top layer 114 comprises a power component 150 (e.g., a battery), a main IC chip 160 a memory device 170 and a bus portion 180.

Although not shown, the components in each layer 112a, 112b, 112c, 114 are interconnected by interconnects formed in or attached to the substrates 122, 126. Examples of suitable interconnects include e.g., embedded fine copper wire, etched silver plating, conductive polymers or flexible circuit boards; all of these interconnections are very flexible and readably available. Although not shown, other components can be included on each layer such as e.g., resistors; Bluetooth circuitry/chip, etc. depending upon the intended use of the patch 110. In addition, an on/off button/switch and/or other buttons/switches can also be present so that the user can e.g., activate/deactivate the electronics, cause the patch 110 to transmit or receive data, etc.

The top layer 114 comprises a main IC chip (or circuit) 160, which may be a programmed processor or a microcontroller and may include at least one low power communication mechanism (e.g., Bluetooth, wireless RF communications, RS-232/RS-432 serial port, USB connector, etc.) for communicating data collected by the patch's electronics to the outside world (discussed below). It should be appreciated that the layers 112a, 112b, 112c, 114 can communicate with each other via wireless communications as well. This would allow the top layer 114 to talk to the lower layers 112a, 112b, 112c to e.g., check stickiness, power levels, or malfunctions of any layer 112a, 112b, 112c. The top layer 114 would have the more expensive wireless technology while the lower layers 112a, 112b, 112c will have "low level" wireless technology to communicate upwards to the top of the stack. Alternatively, the lower layers 112a, 112b, 112c could require the more advanced wireless technology to provide for more robust sensing electronics in those layers.

It should be appreciated that the illustrated main IC chip 160 could comprise one or more chips and/or circuits connected to perform and control the intended function of the patch 110 and to communicate with an external source to input/output any needed data.

The IC chips 140 on the lower layers 112a, 112b, 112c can be programmed processor or microcontrollers that control the activity of the individual layer. These IC chips 140 are connected to the sensors 132, 134, 136, 138 and will collect data from the sensor and pass the data through the bus portion 142 where it can be used by another lower layer or the top layer 114. The IC chip 160 of the top layer 114 can process the data, have it stored in the memory device 170 and/or transmitted externally from the patch 110 using the communication mechanism in or connected to the chip 160. If desired, the main IC chip 160 could be connected to the IC chips 140 in the other layers 112a, 112b, 112c via a suitable interconnect 162. Addressing, data and/or control data can be passed between the thus connected IC chips 140, 160 as desired. In addition, data can be passed between layers 112a, 112b, 112c, 114 using the data bus portions 142, 180. This data can be stored in the memory device 170, which in one embodiment is a flash memory or other type of non-volatile memory device.

In one embodiment, the power component 150 of the main layer 114 powers all of the layers 112a, 112b, 112c, 114. As such, the power components of the lower layers 112a, 112b, 112c merely need to be connections (e.g., a bus) to the power component 150. In another embodiment, each power component 130, 150 is a separate source of power for its layer. The power components 130, 150 in each layer are illustrated as being connected to each other (e.g., in a manner in which multiple batteries may be connected to each other). It should be appreciated, however, that the power components 130, 150 do not have to be connected to each other if they have enough power to power the electronics (i.e., sensors, IC chips, memory, data bus portion, etc.) on their respective layer. As can be appreciated, depending upon its intended duration of use for each layer (e.g., a few hours to one or more days), each patch 110 will have its own unique power requirements that dictate the type of power components 130, 150 used therein. It should be appreciated that the top layer 114 may need a more robust power component because it is the last layer disposed of. Similarly, lower layers 112a, 112b, 112c that are in an upper portion of the stack of lower layers may need a more robust power source than layers that are in the lower portion of the stack.

It should be appreciated that other types of power components besides batteries can be used. For example, the power components could be one or more of solar cells, hydraulic, hybrid, gas, chemical, mechanical, or other power components. It should also be appreciated that that a layer, power component, or other electronics in the patch 110 can be activated e.g., by skin contact, adhesive sticking, adhesive heating and/or removal of the liner that had components (electrical or non-electrical) and which lost contact with the adhesive/stick-to-skin layer, thus turning on that layer in whole or solely parts/portions of that layer. In addition, a layer above another layer may have its power component in the off state because it has not yet been applied to e.g., the user's skin.

As can be appreciated, by stacking multiple adhesive layers on top of each other, more expensive electronic/hardware components can be used on the top layer 114 while less expensive (and more easily disposable) electronic/hardware components can be placed in lower layers 112a, 112b, 112c, which are used and disposed of at regular intervals. This reduces costs because the necessary expensive hardware is not being disposed of after each use of a layer. This also means that more durable electronic/hardware components can be used in the top layer 114 since the top layer 114 is not discarded until the intended usefulness/lifetime of the patch 110 has expired. Likewise, the top layer 114 can comprise more robust power, memory storage and/or communication electronic/hardware components for the same reason. Thus, there will less chance that the patch 110 will malfunction; in addition, the patch 110 can process, store and transmit more data than existing patches.

Although not intended to be limiting, the following are examples of the electronic/hardware components that could be used in the patch 110. Example sensors 132, 134, 136, 138 include off-the-shelf microphones made e.g., by Panasonic (part number WM-64K) and/or accelerometers made e.g., by Analog Devices (part number ADXL362BCCZ). These are inexpensive devices that are suitable for use in the regularly disposable lower layers 112*a*, 112*b*, 112*c*. An example of the power component 150 used in the top layer 114 can include a lithium battery such as e.g., the CR2032 battery by Panasonic. An example of the IC chip 160 used in the top layer 114 can include an MSP430F5528IYFF micro controller by Texas Instrument.

As mentioned above, the patch 110 can collect data (via the sensors 132, 134, 136, 138), process the data and/or store it in the memory device 170 in the top layer 114. The data can be passed between layers 112*a*, 112*b*, 112*c* and to the top layer 114 (via bus portions 142, 180). Thus, with the preservation of IC chip 160 and memory 170 of the top layer 114, data from the disposable lower layers 112*a*, 112*b*, 112*c* is recorded allowing the data to be integrated and more robust data analysis to be performed on the patch 110, if desired. In addition, it is desirable to output the raw or processed data to the "outside" world. Thus, the firmware and embedded software provided in the top layer 114 communicates desired data to an external device (e.g., computer, tablet, smart phone, etc.) or a network/Internet "cloud" using one or more of Bluetooth or other wireless communication or with a hardwired communication mechanism such as e.g., a USB, RS-232 or RS-432 port on the patch 110.

As can be appreciated, there are numerous uses for the patches 10, 110 disclosed herein. As mentioned above, patch 10 can be used as a bandage (e.g., when gauze or other suitable material is contained on/within the layers 12*a*, 12*b*, 12*c*, 14), can be used to apply medicine to treat a wound, infection or a patient's addiction (e.g., when medicine or another substance is contained on/within the layers 12*a*, 12*b*, 12*c*, 14), or can be used as a multi-layer adhesive tape. Patch 110, because it contains electronics/hardware, can be used for at least the following applications: monitoring sleep apnea or other sleeping disorders/problems; monitoring a discharged patient; self-monitoring a person's response to physical activity; and monitoring how a child/baby is breathing. In addition, the patch 110 can be adapted to be used with medical equipment such as e.g., cardio-rhythm devices (e.g., EKG and Holter monitors) and diabetes devices (e.g., artificial pancreas). Moreover, the patch 110 can be used as a digital bandage, providing both a healing function and a health monitoring function at the same time. The patch 110 could be used as a point-of-care fluid reading device where the lower layer is "dirty" thus, protecting top layer from contamination. The patch 110 could be used as point of care devices/analyzers that monitor CBC, minerals, chemical levels. (related to POC type device), etc. The patch 110 could use Bluetooth 'pairing' such that e.g., if children in one family are wearing the patch 110, a parent can monitor their proximity to each other and an alarm can be sounded if one or more of the children stray too far (e.g. this would be useful at a large event). Once again, it should be appreciated that the disclosed patches 10, 110 should not be limited to a particular use and/or construction and that the following examples are merely for illustration purposes.

When used to monitor sleep apnea, or other sleeping disorders, a user could apply a e.g., a 3-day patch 110 having a lower layer 112*a*, 112*b*, 112*c* for each day/night being monitored. The user opens the package, hits the on switch, peels off the liner (if provided) from the lowest layer 112*a*, and sticks the patch 110 on his/her neck. Real-time sleep data (e.g., breathing and body motion) is sent wirelessly to a remote device provided by a doctor or e.g., a smart phone, tablet, or computer using e.g., Bluetooth communications. When the user wakes up, he/she peels off the patch 110 and disposes the lowermost layer 112*a*. The user goes about his/her daily activities and when it is time to go back to sleep, he/she reapplies the patch 110 using the next lower layer (e.g., 112*b*). This process is repeated until the lower layers 112*a*, 112*b*, 112*c*, etc. are used up. In addition to, or alternatively, the monitored data can be stored in the memory device 170 and the top layer 114 can be attached, via a wireless or wired connection, to a device that can download the data from the memory device 170.

The disclosed patch 110 can be used by a hospital to reduce its readmission rate by monitoring a discharged patient for an extended period of time (e.g., 60 days). When used in this type of application, a user is provided with a one or two month patch 110 that is worn continuously for approximately twenty-four hours a day (i.e., the patch 110 is only removed to peel off a lower layer and then reapplied). Real-time results are recorded during the day and sent e.g., to real-time Internet/network cloud associated with the hospital or patient's doctor. The patch 110 is beneficial to the patient because the patient can take a shower without wearing bulky devices (e.g., Halter Monitor) as is presently required. It should be appreciated that long-use patches can be implemented in many ways. For example, a 60-day patch could be implemented as one big patch containing 60/61 layers; alternatively, the patch 110 could be divided into "intervals" (e.g., monthly, weekly, pack of five layers, etc.). It should be appreciated that the uniqueness of the top layer 114 (and its relatively expensive components) may also determine the stack size of the patch 110. Moreover, the patch 110 can be packaged with other patches 110 in the same package/box (e.g., 6 ten-day patches in one package); a digital time stamp could be used to show when one patch 110 can be or was used and then the next patch 110, etc. (i.e., the patches 110 are automatically dated). When multiple patches 110 are to be used, one patch 110 can contain a master top layer 114 while the other patches 110 can contain solely lower layers 112*a*, 112*b*, 112*c* or modified top layers 114 with less electronics than the main top layer 114.

The disclosed patch 110 can be used for self-monitoring of a person's health during physical activity such as jogging or yoga. The user will wear the patch 110 during the activity and then may look at results e.g., real-time on a smart phone/tablet application or a later time on any suitable device. As another example, people showing up for a yoga class can buy the disclosed low-cost patch 110 while also paying for a towel or mat. People use the patch as a way to start new conversations with their coach who can then review data from the patch 110.

As can be appreciated, the patches 110 can be made small enough for a parent to apply them to a baby or small child. This way, the parent can monitor a baby/child's breathing, sleep pattern, and/or asthma. The disclosed patch 110 is also easy to use, even a child could use it on his/her own. It should also be appreciated that the patches 10/110 could include mechanical supports or other material to conform the patch 10/110 to a particular shape such as e.g., a curved shape. For example, the top layer 14/114 could mold or hold the rest of the layers in the stack in the desired shape.

The foregoing examples are provided merely for the purpose of explanation and are in no way to be construed as limiting. While reference to various embodiments is made, the words used herein are words of description and illustration, rather than words of limitation. Further, although reference to particular means, materials, and embodiments are shown, there is no limitation to the particulars disclosed herein. Rather, the embodiments extend to all functionally equivalent structures, methods, and uses, such as are within the scope of the appended claims.

Additionally, the purpose of the Abstract is to enable the patent office and the public generally, and especially the scientists, engineers and practitioners in the art who are not familiar with patent or legal terms or phraseology, to determine quickly from a cursory inspection the nature of the technical disclosure of the application. The Abstract is not intended to be limiting as to the scope of the present inventions in any way.

What is claimed is:

1. A re-usable patch comprising:
   a plurality of removable lower layers, each lower layer having a substrate with a first surface and a second surface, each first surface comprising an adhesive formed thereon, the removable lower layers being configured into a stack, each lower layer comprising a same lower layer electronics as other lower layers in the stack; and
   a top layer provided over a second surface of a topmost lower layer in the stack, said top layer having top layer electronics in communication with the electronics of the lower layers,
   wherein said electronics on the lower layers comprise one or more sensors configured to monitor a same characteristic or activity of a wearer of the patch and comprise electronics configured to communicate the monitored characteristic or activity externally from the patch via the top layer electronics, the one or more sensors of each lower layer being the same as the one or more sensors of each other lower layer,
   wherein each of said lower layers is configured to be removable such that removal of a lower layer removes the electronics of that lower layer and exposes the first surface of a next lower layer in the stack such that the one or more sensors of a lowest one of said lower layers monitor the characteristic or activity of the wearer and the one or more sensors of all other lower layers are inactive, and
   wherein each of said lower layers is configured so that upon removal of a lowest of said lower layers, the one or more sensors of the next lower layer in the stack monitors the characteristic or activity of the wearer and communicates the monitored characteristic or activity externally from the patch via the top layer electronics.

2. The patch of claim 1, further comprising a liner attached to the adhesive of a bottommost layer in the stack.

3. The patch of claim 2, wherein the liner comprises release paper.

4. The patch of claim 1, wherein one or more sensors are configured to monitor one or more of movement, breathing, and biological fluids of the wearer.

5. The patch of claim 1, wherein said lower layer and top layer electronics comprise one or more of microphones, accelerometers, pressure sensors, humidity sensors, temperature sensors, altimeters, electrical sensors, microcontrollers, power source components, data bus components, memory storage devices and communication devices.

6. The patch of claim 5, wherein the power source components comprise solar cells.

7. The patch of claim 5, wherein the communication devices comprise wired or wireless communication devices.

8. The patch of claim 1, wherein at least one of the lower layers comprises a tab configured to assist with removal of the at least one of the lower layers a from the patch.

9. A re-usable patch comprising:
   a plurality of adhesive layers, each adhesive layer comprising a first surface comprising an adhesive and a second surface comprising a non-adhesive material, the plurality of adhesive layers being configured into a stack such that a second surface of a lower layer in the stack is removably adhered to a first surface of an upper layer in the stack, and
   wherein at least two adjacent lower adhesive layers in the stack below a topmost layer in the stack comprise a same set of electronics including one or more sensors configured to monitor data indicative of a characteristic or activity of a wearer of the patch such that the one or more sensors of a lowest one of said at least two adjacent lower adhesive layers monitor the characteristic or activity of the wearer and the one or more sensors of all other lower adhesive layers are inactive and when the lowest one of the at least two adjacent lower adhesive layers including the one or more sensors monitoring the data is removed, the one or more sensors of another one of the at least two adjacent lower adhesive layers monitors the data after the removal, the one or more sensors of each lower layer being the same as the one or more sensors of each other lower layer.

10. The patch of claim 9, wherein the electronics of each adhesive layer are configured to pass data to the electronics on another adhesive layer using a data bus formed across each adhesive layer.

11. The patch of claim 9, wherein the electronics of each adhesive layer are configured to pass data to the electronics on another adhesive layer using wireless communications.

12. The patch of claim 9, wherein said electronics comprise a clock.

13. The patch of claim 9, wherein said electronics comprise a GPS.

14. The patch of claim 9, wherein the topmost layer of the stack comprises a padding.

15. The patch of claim 9, wherein the topmost layer of the stack comprises a component for shaping the patch.

16. The patch of claim 9, wherein the topmost layer of the stack comprises a graphical design or message.

17. A patch comprising:
   a plurality of first layers formed into a stack; and
   a second layer provided over a topmost first layer of the stack,
   wherein each first layer and the second layer comprises a first surface comprising an adhesive and a second surface comprising a non-adhesive substrate, a second surface of a lower first layer in the stack is removably adhered to a first surface of an upper first layer in the stack,
   wherein each first layer comprises at least one sensor and an integrated circuit configured to perform a monitoring function, the at least one sensor of each first layer being the same as the at least one sensor of each other first layer,
   wherein the at least one sensor and the integrated circuit of a lowest one first layer is configured to perform the monitoring function until the lowest one first layer is removed from the stack,
   wherein each at least one sensor of each first layer aside from the lowest one first layer is inactive while the at least one sensor and the integrated circuit of the lowest one first layer performs the monitoring function, and
   wherein, when the lowest one first layer is removed, the at least one sensor and the integrated circuit of a next first layer perform the same monitoring function that the lowest one first layer performed prior to removal.

18. The patch of claim 17, wherein the second layer comprises electronics.

19. The patch of claim 18, wherein the electronics of each first layer are configured to pass data to the electronics on another first layer and the second layer using a data bus formed across each first layer and the second layer.

20. The patch of claim 18, wherein the electronics of each first layer are configured to pass data to the electronics on another first layer and the second layer using wireless communications.

21. The patch of claim 18, wherein said electronics comprise at least one power source selected from the group consisting of batteries, solar cells, hydraulic, hybrid, gas, chemical, and mechanical power sources.

22. The patch of claim 18, wherein said electronics of a first layer are powered by a power source on that first layer and the electronics of the second layer are powered by a power source on the second layer.

23. The patch of claim 18, wherein said electronics of a first layer are powered by a power source on the second layer.

24. The patch of claim 18, wherein said electronics comprise at least one of a clock, GPS, health monitor, and smartphone.

\* \* \* \* \*